United States Patent [19]

Hock et al.

[11] Patent Number: 5,043,346
[45] Date of Patent: Aug. 27, 1991

[54] AMINO ACID ESTERS, PHARMACEUTICALS CONTAINING THEM, AND THE USE THEREOF IN LEARNING DISORDERS

[75] Inventors: Franz Hock, Dieburg; Josef Scholtholt, Hanau; Hansjörg Urbach, Kronberg; Rainer Henning, Hattersheim am Main; Ulrich Lerch, Hofheim am Taunus; Wolf-Ulrich Nickel, Bad Soden am Taunus; Wolfgang Rüger, Kelkheim, all of Fed. Rep. of Germany

[73] Assignee: Hoechst Aktiengesellschaft, Frankfurt am Main, Fed. Rep. of Germany

[21] Appl. No.: 340,656

[22] Filed: Apr. 20, 1989

[30] Foreign Application Priority Data

Apr. 22, 1988 [DE] Fed. Rep. of Germany ....... 3813819

[51] Int. Cl.$^5$ ................. C07D 207/08; C07D 269/02; A61K 31/41
[52] U.S. Cl. .................... 514/409; 548/411; 548/530; 548/452; 514/419; 514/423; 514/412
[58] Field of Search ......... 548/452, 530, 411; 514/412, 419, 409, 423

[56] References Cited

U.S. PATENT DOCUMENTS

| | | | |
|---|---|---|---|
| 4,374,847 | 2/1983 | Gruenfeld | 514/415 |
| 4,508,729 | 4/1985 | Vincent et al. | 514/419 |
| 4,525,301 | 6/1985 | Henning et al. | 548/411 |
| 4,558,064 | 12/1985 | Teetz et al. | 514/409 |
| 4,558,065 | 12/1985 | Urbach et al. | 514/412 |
| 4,562,202 | 12/1985 | Urbach et al. | 514/423 |
| 4,587,258 | 5/1986 | Gold et al. | 514/412 |
| 4,591,598 | 5/1986 | Urbach et al. | 514/412 |
| 4,614,805 | 9/1986 | Urbach et al. | 548/427 |
| 4,620,012 | 10/1986 | Henning et al. | 548/411 |
| 4,624,962 | 11/1986 | Henning et al. | 548/452 |
| 4,659,838 | 4/1987 | Lerch | 548/252 |
| 4,668,796 | 5/1987 | Geiger et al. | 548/452 |
| 4,668,797 | 5/1987 | Urbach et al. | 548/452 |
| 4,684,662 | 8/1987 | Henning et al. | 548/452 |
| 4,691,022 | 9/1987 | Henning et al. | 548/408 |
| 4,714,708 | 12/1987 | Urbach et al. | 514/412 |
| 4,727,160 | 2/1988 | Teetz et al. | 548/452 |
| 4,808,573 | 2/1989 | Gold et al. | 514/19 |
| 4,818,749 | 4/1989 | Gold et al. | 514/19 |
| 4,822,894 | 4/1989 | Geiger et al. | 548/252 |
| 4,831,157 | 5/1989 | Gold et al. | 548/252 |
| 4,849,524 | 7/1989 | Henning et al. | 548/411 |
| 4,868,307 | 9/1989 | Barton et al. | 546/256 |
| 4,886,827 | 12/1989 | Urbach et al. | 514/412 |

OTHER PUBLICATIONS

Leonard et al., J. Am. Chem. Soc., 77, 439 (1955).
Leonard et al., J. Am. Chem. Soc., 78, 3457 (1956).
Leonard et al., J. Am. Chem. Soc., 78, 3463 (1956).
Leonard et al., J. Am. Chem. Soc., 81, 5627 (1959).
Koelsch et al., J. Org. Chem., 26, 1104 (1961).
Griot et al., Helv. Chim. Acta. 42, 121 (1959).
Bonnett et al., J. Chem. Soc., 2087 (1959).
Battersby et al., J. Chem. Soc., 4333 (1958).
Rosenblatt et al., The Chemistry of Functional Groups, Supplement F: The Chemistry of Amino, Nitroso and Nitro Compounds and Their Derivatives, Part II, S. Patai, ed., Wiley & Sons: New York 1982, pp. 1100–1104.
L. W. Haynes, Enamines, A. G. Cook, ed., Marcel Decker, Inc.: 1969, pp. 68–79, 261–269, 413.
Fieser & Fieser, Reagents for Organic Synthesis, vol. 1, pp. 644–651 (1967).
Boehme et al., Iminium Salts in Organic Chemistry, Part I (E. C. Taylor, ed.), Wiley & Sons: New York, 1976, p. 143.
S. Dayagi et al., The Chemistry of Functional Groups. the Chemistry of the Carbon–Nitrogen Double Bond, S. Patai, ed., Wiley & Sons: New York, 1970, p. 119.
W. Greenlee et al., J. Med. Chem., 28, 434–442 (1985).
K. Ogawa et al., J. Chem. Soc., Perkin Trans. I, 3031–3035 (1982).
R. Bacon and D. Stewart, J. Chem. Soc. (C), 1384–1387 (1966).
R. Bacon et al., J. Chem. Soc. (C), 1388–1389 (1966).
Patchett et al., Nature, 288, 280–283 (1980).
Booth et al., Chemistry and Industry, 466–467 (1956).
Booth et al., J. Chem. Soc., Part I, 1050–1054 (1959).
Murakoshi et al., Chemical Abstracts, 61, 9465(e) (1964).
Cushman et al., Fed. Proc., 38 (13), 2778–2782 (1979).
Houben–Weyl, Methoden der Organischen Chemie, 7(2b), 1403–1404 (1976).
Katritskaya, Dzh. Lagorskaya Khimia Geterosikl. Soedin., Moskow 1963, pp. 155–158.
Anderson, Jr. et al., J. Org. Chem., 43(1), 54–57 (1978).
Bertho et al., "Synthesen In Der 2-Azabicyclo[0.3.-3]-octan-Reihe", Chemische Berichte, 92(7), 2218–2235 (1959).
Farkas et al., J. Org. Chem., 22, 1261–1263 (1957).
Taylor et al., J. Org. Chem., 38(16), 2817–2821 (1973).
Taylor et al., Heterocycles, 25, 343–345 (1987).
English language translation of Mitzlaff et al., Liebig's Ann. Chem. 1713–1733 (1978).
Chem. Berichte 86: 1524–1528 (1953).
Quarterly Reviews 25: 323–341 (1971).
Chem. Abst. 49/1955/3009c.

*Primary Examiner*—David B. Springer
*Attorney, Agent, or Firm*—Finnegan, Henderson, Farabow, Garrett and Dunner

[57] ABSTRACT

The invention relates to amino acid esters of the formula I

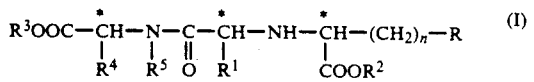

in which n is 2 and R, $R^1$, $R^2$, $R^3$, $R^4$ and $R^5$ have the meaning indicated in the description, to a process and intermediates for the preparation thereof, to agents containing them, and the use thereof.

11 Claims, No Drawings

AMINO ACID ESTERS, PHARMACEUTICALS CONTAINING THEM, AND THE USE THEREOF IN LEARNING DISORDERS

DESCRIPTION

EP-A 243645 discloses the use of ACE inhibitors for the treatment of cognitive dysfunctions.

The invention relates to new amino acid esters of the formula I

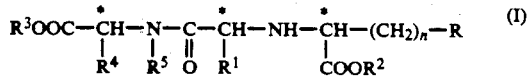

in which n is 2,

R denotes an optionally substituted aliphatic radical having 1-18 carbon atoms, an optionally substituted alicyclic radical having 3-20 carbon atoms, or an optionally substituted aromatic radical having 6-12 carbon atoms, $R^1$ denotes the side-chain, which is protected if necessary, of a naturally occurring α-amino acid of the formula $R^1$—CH(NH$_2$)—COOH, $R^2$ denotes hydrogen, an optionally substituted aliphatic radical having 1-18 carbon atoms, benzyl or an optionally substituted alicyclic radical having 3-20 carbon atoms, $R^3$ denotes hydrogen, an optionally substituted aliphatic radical having 1-18 carbon atoms or an optionally substituted araliphatic radical having 7-20 carbon atoms, and $R^4$ and $R^5$ form, together with the atoms carrying them, a mono-, bi- or tricyclic heterocyclic ring system having 3 to 15 carbon atoms, with the proviso that A: $R^2$ denotes an optionally substituted aliphatic radical having 7-18 carbon atoms or an optionally substituted alicyclic radical having 7-20 carbon atoms, and otherwise n, R, $R^1$, $R^3$, $R^4$ and $R^5$ have the abovementioned meaning, or B: $R^3$ denotes an optionally substituted aliphatic radical having 7-18 carbon atoms or an optionally substituted araliphatic radical having 7-20 carbon atoms, and otherwise n, R, $R^1$, $R^2$, $R^4$ and $R^5$ have the abovementioned meaning, or C: R denotes an optionally substituted aliphatic radical having 9-18 carbon atoms, and otherwise n, $R^1$, $R^2$, $R^3$, $R^4$ and $R^5$ have the abovementioned meaning, and the physiologically tolerated salts thereof, excepting n-octyl 2-[N-(1S ethoxycarbonyl-3-phenylpropyl)-S-alanyl]-(1S,3S,5S)-2-azabicyclo[3.3.0]octane-3-carboxylate, n-octyl 2-N-(1S-carboxyl-3-phenylpropyl)-S-alanyl]-(1S, 3S,5S)-2-azabicyclo[3.3.0]octane-3-carboxylate, and the physiologically tolerated salts thereof.

An optionally substituted aliphatic radical is to be understood to be an aliphatic acyclic radical, i.e. a radical having an open, straight or branched carbon chain, such as, for example, alkyl, alkenyl, alkynyl and corresponding polyunsaturated radicals.

An optionally substituted alicyclic radical is a preferably mono- to pentacyclic isocyclic non-aromatic radical which has single bonds or unsymmetrically distributed double bonds and can also be branched (i.e. carry open-chain aliphatic side-chains) and is linked via a ring carbon atom or a side-chain carbon atom. Several rings as components of a radical of this type are fused-on, spiro-linked or isolated. Examples of radicals of this type are cycloalkyl, cycloalkenyl, bicycloalkyl, tricycloalkyl and radicals derived from mono-, bi- or oligocyclic terpenes, such as menthyl, isomenthyl, bornyl, caranyl, epibornyl, epiisobornyl, isobornyl, norbornyl, neomenthyl, neoisomenthyl, pinanyl and thujanyl; they are preferably unsubstituted (aliphatic side-chains are not substituents according to the present definition).

An optionally substituted aromatic radical is preferably aryl such as henyl, biphenylyl or naphthyl, which is optionally mono-, di- or trisubstituted. Radicals derived from aryl, such as aralkyl, can be substituted like aryl.

An optionally substituted araliphatic radical is to be understood to be, in particular, aralkyl radicals such as arylalkyl, diarylalkyl, indanyl or fluorenyl, in which aryl is as defined above and can be substituted in the manner indicated there.

$R^4$ and $R^5$ can form, with the atoms carrying these, a mono-, bi- or tricyclic heterocyclic ring system having 3 to 15 ring carbon atoms.

Particularly suitable ring systems of these types are those from the following group:
Octahydrocyclopenta[b]pyrrole (D);
Spiro[(bicyclo[2.2.2]octane)-2,3'-pyrrolidine](H);
Pyrrolidine (O); 1,2,3,3a,4,6a-hexahydrocyclopenta[b]pyrrole (P).

The suitable heterocyclic ring systems have the following structural formulae:

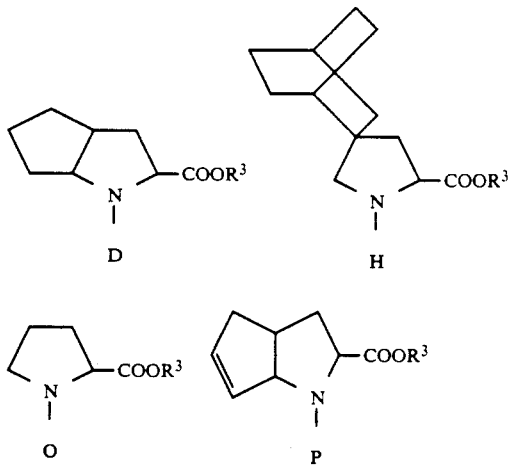

Examples of naturally occurring α-amino acids are Ala, Val, Leu, Ile, Ser, Thr, Asp, Asn, Glu, Gln, Arg, Lys, Hyl, Orn, Cit, Tyr, Phe, Trp and His.

If $R^1$ represents a side-chain of a protected naturally occurring α-amino acid, such as, for example, protected Ser, Thr, Asp, Asn, Glu, Gln, Arg, Lys, Hyl, Cys, Orn, Cit, Tyr, Trp or His, the preferred protective groups are the groups customary in peptide chemistry (cf. Houben-Weyl, Vol. XV/1 and XV/2). In the case where $R^1$ denotes the protected lysine side-chain, the known amino protective groups are preferred, but especially Z, Boc or ($C_1$-$C_6$)alkanoyl. Suitable and preferred as O-protective groups for tyrosine are ($C_1$-$C_6$)alkyl, especially methyl or ethyl.

The compounds of the formula I have asymmetric carbon atoms and can therefore occur as enantiomers and diastereomers. The invention embraces both the pure enantiomers and the racemates.

In the case of compounds of the formula I or II which have several chiral atoms, all possible diastereomers as racemates or enantiomers, or mixtures of various diastereomers, are suitable.

Suitable salts of the compounds of the formula I are, depending on the acidic or basic nature of these compounds, alkali metal or alkaline earth metal salts or salts with physiologically tolerated amines or salts with inorganic or organic acids such as, for example, HCl, HBr, $H_2SO_4$, maleic acid, fumaric acid, tartaric acid and citric acid.

Preferred compounds of the general formula I are those in which n is 2,

R denotes an aliphatic radical having 4–10 carbon atoms, an alicyclic radical having 6 carbon atoms or an aromatic radical having 6 carbon atoms, $R^1$ denotes methyl or benzyl, $R^2$ denotes hydrogen, an aliphatic radical having 1–18 carbon atoms, benzyl or an alicyclic radical having 6–10 carbon atoms, $R^3$ denotes hydrogen, an aliphatic radical having 2–14 carbon atoms or an araliphatic radical having 7–15 carbon atoms, and $R^4$ and $R^5$ form, together with the atoms carrying them, a mono-, bi- or tricyclic heterocyclic ring system having 3–11 carbon atoms, with the proviso that A: $R^2$ denotes an aliphatic radical having 7–18 carbon atoms or an alicyclic radical having 7–10 carbon atoms, and otherwise n, R, $R^1$, $R^3$, $R^4$ and $R^5$ have the abovementioned meaning, or B: $R^3$ denotes an aliphatic radical having 7–14 carbon atoms or an araliphatic radical having 7–15 carbon atoms, and otherwise n, R, $R^1$, $R^2$, $R^4$ and $R^5$ have the abovementioned meaning, or C: R denotes an aliphatic radical having 9 or 10 carbon atoms, and otherwise n, $R^1$, $R^2$, $R^3$, $R^4$ and $R^5$ have the abovementioned meaning, and the physiologically tolerated salts thereof.

Particularly preferred compounds of the general formula are those in which n is 2, R denotes n-butyl, n-decyl, cyclohexyl or phenyl, $R^1$ denotes methyl or benzyl, $R^2$ denotes hydrogen, methyl, ethyl, isobutyl, n-octyl, n-octadecyl, benzyl or menthyl, $R^3$ denotes hydrogen, ethyl, n-octyl, n-nonyl, 5-nonyl, n-decyl, n-tetradecyl, 2-octenyl, 2-octynyl, 3-octynyl, benzyl, benzhydryl or 3,3-diphenylpropyl, and $R^4$ and $R^5$ form, together with the atoms carrying them, a heterocyclic ring system from the series comprising octahydrocyclopenta[b]pyrrole, spiro[(bicyclo[2.2.2]octane)-2,3,-pyrrolidine], pyrrolidine or 1,2,3,3a,4,6a-hexahydrocyclopenta[b],-pyrrole, with the proviso that A: $R^2$ denotes n-octyl, n-octadecyl or menthyl, and otherwise n, R, $R^1$, $R^3$, $R^4$ and $R^5$ have the above-mentioned meaning, or B: $R^3$ denotes n-octyl, n-nonyl, 5-nonyl, n-decyl, n-tetradecyl, 2-octenyl, 2-octynyl, 3-octynyl, benzhydryl or 3,3-diphenylpropyl, and otherwise n, R, $R^1$, $R^2$, $R^4$ and $R^5$ have the abovementioned meaning, or C: R denotes n-decyl, and otherwise n, $R^1$, $R^2$, $R^3$, $R^4$ and $R^5$ have the stated meaning, and the physiologically tolerated salts thereof.

Very particularly preferred are the following compounds of the formula I, and the physiologically tolerated salts thereof.

n-Octyl 2-[N-(1S-ethoxycarbonyl-n-heptyl)-S-alanyl]-(1S, 3S,5S)2-azabicyclo[3.3.0 ]octane-3-carboxylate;

n-Octyl 2-[N-(1S-ethoxycarbonyl-3-cyclohexylpropyl)-S-alanyl]-(1S,3S,5S)-2-azabicyclo[3.3.0]octane-3carboxylate;

Benzyl 2-[N-(S-ethoxycarbonyl-n-tridecyl)-S-alanyl](1S,3S,5S)-2-azabicyclo[3.3.0]octane-3-carboxylate;

Benzyl 2-[N-(1R-ethoxycarbonyl-n-tridecyl)-S-alanyl]-(1S, 3S,5S)-2-azabicyclo[3.3.0]octane-3-carboxylate;

n-Decyl 2-[N-(1S-ethoxycarbonyl-3-phenylpropyl)-S-alanyl]-(1S,3S,5S)-2-azabicyclo[3.3.0]octane-3carboxylate;

5-Nonyl 2-[N-(1S-ethoxycarbonyl-3-phenylpropyl)-S-alanyl]-(1S,3S,5S)-2-azabicyclo[3.3.0]octane-3-carboxylate;

n-Octyl 2-[N-(1S-isobutyloxycarbonyl-3-phenylpropyl)-S-alanyl]-(1S,3S,5S)-2-azabicyclo[3.3.0]octane-3carboxylate;

2-[N-(1S-n-octyloxycarbonyl-3-phenylpropyl)-S-alanyl](1S,3S,5S)-2-azabicyclo[3.3.0]octane-3-carboxylic acid;

Ethyl 2-[N-(1S-n-octyloxycarbonyl-3-phenylpropyl)-S-alanyl]-(1S,3S,5S)-2-azabicyclo[3.3.0]octane-3carboxylate;

n-Octyl 2-[N-(1S-n-octyloxycarbonyl-3-phenylpropyl)-S-alanyl]-(1S,3S,5S)-2-azabicyclo[3.3.0]octane-3-carboxylate;

Benzyl 2-[N-(1S-n-octadecyloxycarbonyl-3-phenylpropyl)-S-alanyl]-(1S,3S,5S)-2-azabicyclo[3.3.0]octane-3-carboxylate;

n-Octyl 2-[N-(1S-n-octadecyloxycarbonyl-3-phenylpropyl)-S-alanyl]-(1S,3S,5S)-2-azabicyclo[3.3.0]octane-3-carboxylate;

Benzyl 2-[N-(1S-menthyloxycarbonyl-3-phenylpropyl)-S-alanyl]-(1S,3S,5S)-2-azabicyclo[3.3.0]octane-3carboxylate;

Benzhydryl 2-[N-(1S-menthyloxycarbonyl-3-phenylpropyl)-S-alanyl]-(1S,3S,5S)-2-azabicyclo[3.3.0]octane-3-carboxylate;

n-Octyl 2-[N-(1S-carboxy-3-phenylpropyl)-S-alanyl](1S,3S,5S)-2-azabicyclo[3.3.0]octane-3-carboxylate;

n-Octyl 2-[N-(1S-ethoxycarbonyl-3-phenylpropyl)-S-alanyl]-(1S,3S,5S)-2-azabicyclo[3.3.0]-7-octene-3carboxylate;

N-[N-(1S-ethoxycarbonyl-3-phenylpropyl)-S-alanyl]-S-proline n-octyl ester;

n-Octyl 2-[N-(1S-methoxycarbonyl-3-phenylpropyl)-S-alanyl]-(1S,3S,5S)-2-azabicyclo[3.3.0]octane-3carboxylate;

n-Octyl 2-[N-(1S-benzyloxycarbonyl-3-phenylpropyl)-S-alanyl]-(1S,3S,5S)-2-azabicyclo[3.3.0]octane-3carboxylate;

n-Decyl 2-[N-(1S-carboxy-3-phenylpropyl)-S-alanyl](1S,3S,5S)-2-azabicyclo[3.3.0]octane-3-carboxylate.

The invention also relates to a process for the preparation of compounds of the formula I, which comprises a) reacting a compound of the formula XIV $$R-(CH_2)_n-\underset{COOQ^2}{\overset{*}{C}H}-NH-\underset{R^1}{\overset{*}{C}H}-\underset{O}{\overset{}{C}}-\underset{R^5}{N}-\underset{R^4}{\overset{*}{C}H}-COOQ^3 \quad (XIV)$$

with a compound of the formula XV $$Q=Y \quad (XV)$$

where R, $R^1$, $R^4$, $R^5$ and n in the abovementioned formulae XIV and XV have the same meaning as in formula I, and i. $Q^2$ is defined as $R^2$ in formula I but does not denote hydrogen, or represents a carboxyl protective group which can easily be eliminated by base, acid or hydrogenolysis, $Q^3$ denotes hydrogen, Y denotes hydroxyl or a leaving group which can be displaced nucleophilically, and Q is defined as $R^3$ in formula I but does not denote hydrogen, or Y denotes $$=\overset{(+)}{N}=\overset{(-)}{N}$$

and

Q denotes an alkylidene radical having 1 to 18 carbon atoms, or ii. $Q^2$ denotes hydrogen, $Q^3$ is defined as $R^3$ in formula I but does not denote hydrogen, or represents a carboxyl protective group which can easily be eliminated by base, acid or hydrogenolysis, Y denotes hydroxyl or a leaving group which can be displaced nucleophilically, and Q is defined as $R^2$ in formula I but does not denote hydrogen, or Y denotes $$=\overset{(+)}{N}=\overset{(-)}{N},$$

and

Q denotes an alkylidene radical having 1 to 18 carbon atoms, or comprises b) reacting a compound of the formula IX $$R-(CH_2)_n-\underset{COOR^2}{\overset{*}{C}H}-OSO_2CF_3 \quad (IX)$$

in which R, $R^2$ and n have the same meaning as in formula I, with a compound of the formula X $$R^3OOC-\underset{R^4}{\overset{*}{C}H}-\underset{R^5}{N}-\underset{O}{\overset{}{C}}-\underset{R^1}{\overset{*}{C}H}-NH_2 \quad (X)$$

in which $R^1$, $R^3$, $R^4$ and $R^5$ have the same meaning as in formula I, or comprises c) reacting a compound of the formula XI $$R^3OOC-\underset{R^4}{\overset{*}{C}H}-\underset{R^5}{NH} \quad (XI)$$

in which $R^3$, $R^4$ and $R^5$ have the same meaning as in formula I, with a compound of the formula XII $$HOOC-\underset{R^1}{\overset{*}{C}H}-NH-\underset{COOR^2}{\overset{*}{C}H}-(CH_2)_n-R \quad (XII)$$

in which n, R, $R^1$ and $R^2$ have the same meaning as in formula I, in analogy to known peptide-coupling processes, and where $Q^2$ or $Q^3$ in the compound obtained in this way represents a protective group which can be eliminated by base, acid or hydrogen-olysis, this protective group being eliminated, where appropriate by treatment with a base or an acid or by hydrogenation, and the compound of the rala I obtained in the above manner optionally being converted into the physiologically tolerated salt thereof.

An alkylidene radical has the formula $$=C\begin{matrix}R^6\\R^7\end{matrix}$$

in which $R^6$ and $R^7$ are as defined below in process variant $a_5$).

According to process variant a), preferably $a_1$) a compound of the formula II $$R-(CH_2)_n-\underset{COOQ^2}{\overset{*}{C}H}-NH-\underset{R^1}{\overset{*}{C}H}-\underset{O}{\overset{}{C}}-\underset{R^5}{N}-\underset{R^4}{\overset{*}{C}H}-COOH \quad (II)$$

in which R, $R^1$, $Q^2$, $R^4$, $R^5$ and n have the same meaning as in formula XIV, is reacted with a compound of the formula III $$R^3-OH \quad (III)$$

in which $R^3$ has the same meaning as in formula I, except that of hydrogen, using esterification methods familiar to those skilled in the art (see, for example, Buehler, Pearson, Survey of Organic Synthesis, Vol. 1, New York 1970, pages 802-825; Houben-Weyl, Methoden der Organischen Chemie (Methods of Organic Chemistry), volume E5, 1985, pages 656-773), for example with acid catalysis or after activation of the carboxyl group of II or the hydroxyl group of III, in particular under the conditions of a Mitsunobu reaction, in a suitable solvent at a temperature up to the boiling point of the reaction mixture, or $a_2$) a compound of the formula II in which R, $R^1$, $Q^2$, $R^4$, $R^5$ and n have the same meaning as in formula XIV is reacted with a compound of the formula IV $$R^3-X \quad (IV)$$

in which $R^3$ has the same meaning as in formula I, except that of hydrogen, and in which X denotes a leaving group which can be displaced nucleophilically, in particular a Cl, Br or I atom or a sulfonic acid residue, under the conditions of a nucleophilic substitution, preferably in a polar organic solvent such as an alcohol, preferably methanol, ethanol, propanol or isopropanol, or a lower ketone, preferably acetone, methyl ethyl ketone or methyl isobutyl ketone, or in acetonitrile, dimethylformamide, dimethyl sulfoxide or sulfolane, or a hydrocarbon, preferably toluene, with or without the presence of an auxiliary base to trap the acid which is formed, preferably in the presence of potassium bicarbonate, potassium carbonate, sodium bicarbonate, sodium carbonate, triethylamine, pyridine, 1,5-diazabicyclo[5.4.0]undec-5-ene or 1,5-diazabicyclo-[4.3.0]non-5-ene, and with or without the presence of an alkali metal halide, preferably sodium iodide or potassium iodide, at a temperature between −50 and +100° C., preferably between −20° and +60° C., or a3) a compound of the formula V

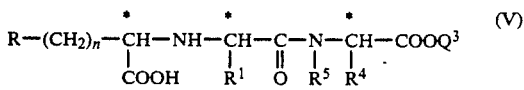

in which R, $R^1$, $Q^3$, $R^4$, $R^5$ and n have the same meaning as in formula XIV, is reacted with a compound of the formula VI

in which $R^2$ has the same meaning as in formula I, except that of hydrogen, as described above under a1), or a4) a compound of the formula V in which R, $R^1$, $Q^3$, $R^4$ and n have the same meaning as in formula XIV is reacted with a compound of the formula VII

in which $R^2$ has the same meaning as in formula I, except that of hydrogen, and in which X has the same meaning as in formula IV, as described above under a2), or a5) a compound of the formula II or V is reacted with a diazoalkane of the formula (VIII)

in which $R^6$ denotes a radical $C_xH_{2x+1}$, and $R^7$ denotes a radical $C_yH_{2y+1}$, x and y are each an integer from 0 to 17, and $x+y \leq 17$, in an inert organic solvent at temperatures between −80° C. and the boiling point of the solvent.

The reaction according to variant b) is carried out, for example, in analogy to the procedure described in U.S. Pat. No. 4525301, in a suitable solvent at a temperature up to the boiling point of the reaction mixture.

Procedure c) is carried out, for example, in analogy to known peptide-coupling processes in an organic solvent such as DMF, $CH_2Cl_2$ or DMA in the presence of aids to coupling, such as carbodiimides (for example dicyclohexylcarbodiimide), diphenylphosphoryl azide, alkanephosphonic anhydrides, dialkylphosphinic anhydrides or N,N-succinimidoyl carbonate, in a solvent such as, for example, acetonitrile or after activation of the compounds of the formula XI, for example by reaction with tetraethyl diphosphite, or after activation of the compounds of the formula XII to active esters (for example with 1-hydroxybenzotriazole), to mixed anhydrides (for example with chloroformic esters), to azides or to carbodiimide derivatives (cf. Schroder, Lubke, The Peptides, volume 1, New York 1965, pages 76-136) at temperatures preferably between −20° C. and the boiling point of the solvent. A protective group which can be eliminated by hydrogenolysis is eliminated by hydrogenolysis on a suitable catalyst such as, for example, palladium on active charcoal under a pressure of 0.2 to 10 bar and at a temperature between 0° C. and 100° C. in an organic solvent to give a compound of the formula I ($R^3=H$).

An easily hydrolyzable aliphatic radical can be eliminated using hydrolysis methods familiar to those skilled in the art (see, for example, Houben/Weyl, Methoden der Organischen Chemie, volume E 5/1, pages 223-255), for example by acid or alkali hydrolysis with formation of the free carboxyl group.

The invention also relates to compounds of the formula XI in which $R^3$ denotes n-octyl, n-nonyl, 5-nonyl, n-decyl, n-tetradecyl, 2-octenyl, 2-octynyl, 3-octynyl, benzyl, benzhydryl or 3,3-diphenylpropyl, and $R^4$ and $R^5$ form, together with the atoms carrying them, a heterocyclic ring system from the series comprising octahydrocyclopenta[b]pyrrole, spiro[(bicyclo-[2.2.2]octane-2,3'-pyrrolidine], pyrrolidine or 1,2,3,3a,4-,6a-hexahydrocyclopenta[b]pyrrole, excepting n-octyl (1S,3S,5S)-2-azabicyclo[3.3.0]octane-3-carboxylate, as well as the physiologically tolerated salts thereof, and to a process for the preparation of these compounds, which comprises reacting a compound of the formula XI in which $R^4$ and $R^5$ are defined as in formula XI, and $R^3$ denotes hydrogen, in analogy to the abovementioned process variant a), with a compound of the formula XV in which Q is defined as $R^3$ in formula XI, but does not denote hydrogen, and Y denotes hydroxyl or a leaving group which can be displaced nucleophilically.

Compounds of the formula II and V are known (see, for example, EP-A 79022, EP-A 105102, EP-A 113880, EP-A 116270, EP-A 74164, EP-A 90362) or can be prepared by analogous routes.

Compounds of the formula III, IV, VI, VII and VIII are known, and most of them can be bought.

Compounds of the formula IX are obtained from compounds of the formula XIII

in which R, $R^2$ and n have the same meaning as in formula in which R, $R^2$ and n have the same meaning as in formula I, by conversion of the hydroxyl group into the $-OSO_2CF_3$ group by conventional processes.

Compounds of the formula X are dipeptides which can be built up from the individual amino acid components by methods of peptide chemistry known per se (see, for example, Houben-Weyl, Methoden der Organischen Chemie, vol. XV, part II, pages 1-364).

Compounds of the formula XI, XII and XIII are known or can be prepared by routes analogous to those for the known compounds.

The compounds of the formula I and the physiologically tolerated salts thereof have a nootropic effect, i.e. improving cognitive function. They are therefore suitable for the treatment of cognitive dysfunctions of various etiologies as occur, for example, in Alzheimer's disease or senile dimentia. The nootropic effect of the compounds according to the invention was tested in the inhibitory (passive) avoidance test (step-through model) on mice with a body weight of 20–25 g. A modified form of the test method described by J. KOPP, Z. BODANECKY and M.E. JARVIK has been described by J. BURES, O. BURESOVA and J. HUSTON in "Techniques and Basic Experiments for the Study of Brain and Behavior", Elsevier Scientific Publishers, Amsterdam (1983).

According to the statements in this literature, a substance is designated as having nootropic activity when it is able to abolish the amnesia produced in the experimental animals by means of an electroconvulsive shock or the amnesia induced by scopolamine.

The experiments were carried out by modified test methods. The comparison compound used was the known nootropic agent 2-oxo-1-pyrrolidinylacetamide according to the invention over the comparison substance was evident from the fact that it is possible to abolish the scopolamine-induced amnesia in the inhibitory avoidance test with an oral MED (minimal effective dose) of 0.03–30 mg/kg. The comparison substance has an oral MED of about 500–1000 mg/kg.

The invention therefore also relates to the use of the compounds according to the invention for the treatment and prophylaxis of cognitive dysfunctions.

The invention additionally embraces pharmaceuticals containing the said compounds, processes for the preparation thereof, and the use of the compounds according to the invention for the preparation of pharmaceuticals which are used for the treatment and prophylaxis of the above-mentioned diseases.

The method according to the invention can be practiced by administering the compounds of the formula I described above to mammals such as monkeys, dogs, cats, rats, humans etc.

The pharmaceuticals are prepared by processes which are known per se and familiar to those skilled in the art. As pharmaceuticals, the pharmacologically active compounds (=active substance) according to the invention are used either as such or, preferably, in combination with suitable pharmaceutical auxiliaries in the form of tablets, coated tablets, capsules, suppositories, emulsions, suspension or solutions, with the content of active substance being up to about 95%, advantageously between 10 and 75%.

The particular auxiliaries suitable for the desired pharmaceutical formulation are familiar to those skilled in the art on the basis of their expert knowledge. Besides solvents, gel-formers, suppository bases, tablet auxiliaries and other active substance vehicles, it is possible to use, for example, antioxidants, dispersing agents, emulsifiers, antifoam agents, flavorings, preservatives, solubilizers or colorants.

The active substances can be administered, for example, onto the mucous membranes (for example orally or rectally) or parenterally (for example intravenously or subcutaneously), with oral administration being preferred.

For a form for oral administration, the active compounds are mixed with the additives suitable for this purpose, such as excipients, stabilizers or inert diluents, and converted by the customary methods into a suitable dosage form, such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, lactose, glucose or starch, especially corn starch. This preparation can be carried out both as dry and as wet granules. Examples of suitable oily excipients or solvents are vegetable or animal oils, such as sunflower oil or fish liver oil.

For subcutaneous or intravenous administration, the active compounds, or the physiologically tolerated salts thereof, are converted into a solution, suspension or emulsion, if desired with the substances customary for this purpose, such as solubilizers, emulsifiers or other auxiliaries. Examples of suitable solvents are water, physiological saline solution or alcohols, for example ethanol, propanol or glycerol, as well as sugar solutions such as glucose or mannitol solutions, or else a mixture of the various solvents mentioned.

The examples which follow are intended to explain the compounds and processes according to the invention without confining the invention to the substances mentioned here as representative.

A. INTERMEDIATES

1)

2-[N-(1S-Isobutyloxycarbonyl-3-phenylpropyl)-S-alanyl]-(1S,3S,5S)-2-azabicyclo[3.3.0]octane-2-carboxylic acid 1a) Isobutyl 2R-hydroxy-4-phenylbutyrate 8 g (44 mmol) of 2R-hydroxy-4-phenylbutyric acid are stirred together with 100 ml of saturated isobutanol/HCl solution at room temperature for 5 hours, the mixture is concentrated, the residue is taken up in ether, and the solution is washed with water, saturated NaHCO$_3$ solution and again with water, dried and concentrated.

Yield: 9.35 g (89%) $[\alpha]_D^{25} = -8.1°$ (c=1, CH$_3$OH)

The following are obtained analogously:
Ethyl 2(RS)-hydroxytetradecanoate;
Ethyl 2(RS)-hydroxyoctanoate;
Methyl 2R-hydroxy-4-phenylbutyrate.

1b) Isobutyl 4-phenyl-2R-(trifluoromethylsulfonyloxy)-butyrate 11.28 g (40 mmol) of trifluoromethanesulfonic anhydride are slowly added at −10° C. to 8.8 g (37.6 mmol) of the hydroxy ester from Example 1a) and 3.2 ml (40 mmol) of pyridine in 200 ml of absolute methylene chloride, and the mixture is then stirred at −10° C. for 10 minutes and at room temperature for 30 minutes. The reaction solution is concentrated, the residue is dissolved in cyclohexane/ethyl acetate 95/5, filtered and purified by column chromatography on 320 g of silica gel (mobile phase cyclohexane/ethyl acetate 95/5).

Yield: 11.85 g (86%).

The following are obtained analogously:
Ethyl 2(RS)-(trifluoromethylsulfonyloxy)octanoate;
Ethyl 2(RS)-(trifluoromethylsulfonyloxy)tetradecanoate;
n-Octyl 4-phenyl-2R-(trifluoromethylsulfonyloxy)butyrate;
n-Octadecyl 4-phenyl-2R-(trifluoromethylsulfonyloxy)-butyrate;
Menthyl 4-phenyl-2R-(trifluoromethylsulfonyloxy)butyrate;
Ethyl 4-phenyl-2(RS)-(trifluoromethylsulfonyloxy)butyrate;
Methyl 4-phenyl-2R-(trifluoromethylsulfonyloxy)butyrate;

Benzyl 4-phenyl-2R-2R-(trifluoromethylsulfonyloxy)-butyrate.

1c) Benzyl 2-N-(1S-isobutyloxycarbonyl-3-phenylpropyl)-S-alanyl]-(1S,3S,4S)-2-azabicyclo[3.3.0]octane-3-carboxylate 13.85 g (32.2 mmol) of benzyl N-(S-alanyl)-(1S,3S,5S)-2azabicyclo[3.3.0]octane-3-carboxylate trifluoroacetate (see Example 3) and 8.7 ml (64.4 mmol) of absolute triethylamine are dissolved in 85 ml of absolute methylene chloride and, at 0° C., a solution of 11.85 g of the triflate from Example 1b) (32.2 mmol) in 85 ml of absolute methylene chloride is added dropwise. The mixture is then stirred at room temperature for 4 hours, the organic phase is extracted by shaking with water three times, dried and concentrated, and the residue (13.4 g) is chromatographed on 800 g of silica gel (mobile phase: cyclohexane/ethyl acetate 7:3 and 1:1, then toluene/ethanol) to remove byproducts.

Yield: 9.65 g (56%) of oily product
$[\alpha]_D^{25} = -39.3°(c=1, \text{methanol})$ 1d) 2-[N-(1S-Isobutyloxycarbonyl-3-phenylpropyl)-S-alanyl]-(1S,3S,5S)-2-azabicyclo[3.3.01]octane-3-carboxylic acid 4.0 g (7.5 mmol) of the benzyl ester from Example 1c) in 220 ml of ethanol are hydrogenated on 0.6 g of palladium/charcoal (10%) within 30 minutes at room temperature. The catalyst is filtered off with suction, and the filtrate is evaporated to dryness.

Yield: 3.32 g (100%) of oily product
$[\alpha]_D^{25} = +6.8°(c=1, \text{methanol})$.

The following are obtained analogously:
2-[N-(1S-Ethoxycarbonyl-n-heptyl)-S-alanyl]-(1S,3S,5S)2-azabicyclo[3.3.0]octane-3-carboxylic acid
2-[N-(1R-Ethoxycarbonyl-n-heptyl)-S-alanyl]-(1S,3S,5S)2-azabicyclo[3.3.0]octane-3-carboxylic acid
2[N-(1S-Ethoxycarbonyl-3-phenylpropyl)-S-alanyl]-(1R,3R,5R)-2-azabicyclo[3.3.0]octane-3-carboxylic acid;

2) n-Octyl 2R-hydroxy-4-phenylbutyrate 9.0 g (50 mmol) of 2R-hydroxy-4-phenylbutyric acid are dissolved in 250 ml of absolute dimethylformamide, 10.0 g (0.1 mmol) of potassium bicarbonate are added, and the mixture is stirred at 50° C. for one hour. After cooling to room temperature, a solution of 15.4 g (80 mmol) of 1bromooctane in 150 ml of absolute dimethylformamide is added dropwise, and the mixture is stirred at 50° C. for three hours. The reaction solution is diluted with 1200 ml of water and extracted three times with ethyl acetate, the combined organic phases are extracted by shaking twice with water, dried over magnesium sulfate and evaporated in a rotary evaporator, and the crude product (21.3 g) is purified by chromatography on 480 g of silica gel (mobile phase methylene chloride/ethyl acetate 100/0, 99:1, 95:5).

Yield: 13.4 g (92%) of oily product.
$[\alpha]_D^{25} = -6.3°(c=2, \text{methanol})$ The following are obtained analogously:
n-Octadecyl 2R-hydroxy-4-phenylbutyrate, melting point 42°-43° C.
Benzyl 2R-hydroxy-4-phenylbutyrate.

3) Benzyl 2-(S-alanyl)-(1S,3S,5S)-2-azabicyclo[3.3.0]octane-3-carboxylate trifluoroacetate 3a) Benzyl 2-(N-tert.butoxycarbonyl-S-alanyl)-(1S,3S,5S)-2-azabicyclco[3.3.0]octane-3-carboxylate 61.5 g (0.251 mol) of benzyl (1S,3S,5S)-2-azabicyclo[3.3.0]octane-3-carboxylate, 47.5 g (0.251 mol) of BOC-L-alanine and 173 ml (1.26 mol) of absolute triethylamine are dissolved in 1025 ml of absolute dimethylformamide, 252 ml of a 50% strength dichloromethane solution of propanephosphonic anhydride are added dropwise at $-5°$ C., and the mixture is stirred at $-5°$ C. for 30 minutes and at room temperature for four hours. The reaction solution is partitioned between water and ethyl acetate, the aqueous phase is extracted once more with ethyl acetate, and the combined organic phases are washed with saturated sodium bicarbonate solution, 10% strength citric acid solution, water and saturated sodium chloride solution, dried and concentrated.

Yield: 93.2 g (39%) of oily product.

3b) Benzyl 2-(S-alanyl)-(1S,3S,5S)-2-azabicyclo[3.3.0]-octane-3-carboxylate trifluoroacetate 235 ml of absolute trifluoroacetic acid are poured onto 93.2 g (0.224 mol) of the BOC derivative from Example 3a) at 0⅓ C., and the mixture is stirred at 0° C. for 2.5 hours. Excess acid is evaporated off in vacuo at 25° C., and the residue is crystallized from 1000 ml of absolute diisopropyl ether.

Yield: 82.6 g (86%), melting point 148°-150° C.

4) N-(1R-Ethoxycarbonyl-3-phenylpropyl)-R alanine

4a) N-(1R-Ethoxycarbonyl-3-phenylpropyl)-R-alanine benzyl ester 6.07 g (60 mmol) of absolute triethylamine and a solution of 10.2 g (30 mmol) of ethyl 3-phenyl-2(RS)-(trifluoromethylsulfonyloxy)butyrate are successively added drop-wise at 0° C. to a solution of 10.5 g (30 mmol) of D-alanine benzyl ester p-toluenesulfonate in 300 ml of absolute methylene chloride. The reaction mixture is stirred at 0° C. for 10 minutes and at room temperature for 2.5 hours, diluted with methylene chloride, washed three times with water, dried and concentrated, and the crude product (11.6 g) is fractionated into the diastereomers by flash chromatography on 770 g of silica gel (mobile phase cyclohexane/ethyl acetate 9:1).

The following are obtained successively:
4.78 g (45%) of the RS diastereomer,
$[\alpha]_D^{25} = +20.8°$ (c=1, methanol)
3.07 g (29%) of the RR diastereomer,
$[\alpha]_D^{25} = +19.7°$ (c=1, methanol).

The following are obtained analogously:
N-(1S-Ethoxycarbonyl-3-phenylpropyl)-S-alanine benzyl ester,
$[\alpha]_D^{25} = -18.4°$ (c=1, methanol);
N-(1R-Ethoxycarbonyl-3-phenylpropyl)-S-alanine benzyl ester,
$[\alpha]_D^{25} = -21.7°$ (c=1, methanol);
N-(1S-Ethoxycarbonyl-n-heptyl)-S-alanine benzyl ester,
$[\alpha]_D^{25} = -31.2°$ (c=1, methanol);
N-(1R-Ethoxycarbonyl-n-heptyl)-S-alanine benzyl ester;

N-(1S-Ethoxycarbonyl-n-tridecyl)-S-phenylalanine benzyl ester;

N-(1(RS)-Ethoxycarbonyl-n-tridecyl)-S-phenylalanine benzyl ester;

4b) N-(1R-Ethoxycarbonyl-3-phenylpropyl)-R-alanine 3.0 g (8.12 mmol) of the RR diastereomer from Example 4a) are dissolved in 75 ml of ethanol and hydrogenated on 250 mg of palladium/charcoal (10%) at room temperature for one hour. The catalyst is filtered off with suction and the filtrate is concentrated.

Yield: 2.2 g (96%) of colorless crystals,
melting point 146°–148° C.

The following are obtained by an analogous route:

N-(1S-Ethoxycarbonyl-3-phenylpropyl)-S-alanine, melting point: 134°–136° C.;

N-(1R-Ethoxycarbonyl-3-phenylpropyl)-S-alanine, melting point: 133°–135° C.;

N-(1S-Ethoxycarbonyl-3-phenylpropyl)-S-alanine, melting point: 148°–150° C.;

N-(1S-Ethoxycarbonyl-n-heptyl)-S-alanine, $[\alpha]_D^{20} = +9.2°$ (c=1, methanol);

N-(1R-Ethoxycarbonyl-n-heptyl)-S-alanine, melting point: 122–124° C.;

N-(1S-Ethoxycarbonyl-n-tridecyl)-S-phenylalanine. melting point: 116–118° C.;

N-(1(RS)-Ethoxycarbonyl-n-tridecyl)-S-phenylalanine, melting point: 87–90° C.;

5) Benzyl 2[N-(1S-ethoxycarbonyl-n-heptyl)-S-alanyl]-(1S,3S,5S)-2-azabicyclo[3.3.01]octane-3-carboxylate 6.0 ml of absolute triethylamine and 8.2 ml of a 50% strength solution of propanephosphonic anhydride in methylene chloride are successively added dropwise at −8° C. to a solution of 2.3 g (8.9 mmol) of N-(1S-ethoxy-carbonyl-n-heptyl)-S-alanine and 2.8 g (10.0 mmol) of benzly (1S,3S,5S)-2-azabicyclo[3.3.0]octane-3-carboxylate in 110 ml of absolute dimethylformamide. The reaction solution is left to stand at room temperature over the week-end and is diluted with ethyl acetate, washed with saturated sodium carbonate solution, 10% strength citric acid solution and saturated sodium chloride solution, dried and concentrated, and the residue (3.9 g) is purified by chromatography on silica gel (mobile phase cyclohexane/ethyl acetate 7:3).

Yield: 1.2 g (28%) of oily product,
$[\alpha]_D^{25} = -46.6°$ (c=1, methanol).

The following are obtained by an analogous route:

Benzyl 2-[N-(1R-ethoxycarbonyl-n-heptyl)-S-alanyl](1S,3S,5S)-2-azabicyclo[3.3.0]octane-3-carboxylate;

$[\alpha]_D^{25} = -32.5°$ (c=0.79, methanol),

Benzyl 2-[N-(1S-ethoxycarbonyl-3-phenylpropyl))-S-alanyl]-(1R,3R,5R)-2-azabicyclo[3.3.0]octane-3carboxylate; $[\alpha]_D^{25} = -1.9°$ (c=1, methanol)

6) n-Octyl (1S,3S,5S)-2-azabicyclo[3.3.01]octane-3-carboxylate

6a) Benzyl 2-tert.butyloxycarbonyl-(1S,3S,5S)-2-azabicyclo[3.3.-0]octane-3-carboxylate A solution of 39.2 g (0.18 mmol) of di-tert.butyl dicarbonate in 60 ml of absolute methylene chloride is slowly added dropwise at 0° C. to a solution of 40.0 g (0.163 mmol) of benzyl (1S,3S,5S)-2 azabicyclo[3.3.0]-octane-3-carboxylate and 23.4 ml (0.169 mol) of absolute triethylamine in 300 ml of absolute methylene chloride, and the mixture is stirred at 0° C. for 15 minutes and at room temperature for one hour. The reaction solution is washed with 10% citric acid solution, saturated sodium bicarbonate solution and water, dried and concentrated.

Yield: 55.6 g of oily product,
$[\alpha]_D^{25} = -1.2°$ (c=2, methanol).

6b) 2-tert.Butyloxycarbonyl-(1S,3S,5S)-2-azabicyclo[3.3.-0]octane-3-carboxylic acid 55.6 g (0.161 mol) of the benzyl ester from Example 6a) in 2 l of ethanol are hydrogenated on 4 g of palladium/ charcoal (10%) at room temperature for 2.5 hours. The catalyst is filtered off with suction, and the filtrate is concentrated.

Yield: 37.3 g (90%);
$[\alpha]_D^{25} = +22.7°$ (c=1, methanol).

6c) n-Octyl 2-tert.butyloxyzarbonyl-(1S,3S,5S)-2-azabicyclo[3.3.-0]octane-3-carboxylate 32.3 g (0.127 mol) of the acid from Example 6b) and 25.3 g (0.253 mol) of potassium bicarbonate are stirred in 500 ml of dimethylformamide at 40° C. for 1.5 hours. After cooling, 48.9 g (0.253 mol) 1-bromooctane are added dropwise, and the mixture is stirred at room temperature overnight. The reaction mixture is poured into water, extracted three times with ethyl acetate, the combined organic phases are washed with saturated sodium bicarbonate solution and water, dried and concentrated, and the crude product (44.3 g) is purified by flash chromatography in two portions on silica gel (900 g, mobile phase toluene/ethanol 95:5 and 99.5:0.5).

Yield: 35.4 g (76% of oily product,
$[\alpha]_D^{25} = +5.7°$ (c=1, methanol).

The following are obtained by an analogous route:

n-Octyl 2-tert.butyloxycarbonyl-(1RS,3RS,5RS)-2azabicyclo[3.3.0]-7-octene-3-carboxylate;

N-tert.butyloxycarbonyl-S-proline n-octyl ester 6d) n-Octyl 1S,3S,5S)-2-azabicyclo[3.3.0]octane-3-carboxylate 2.6 g (7.0 mmol) of the BOC compound from Example 6c) are stirred with 9 ml of trifluoroacetic acid at 0° C. for 1.5 hours. The excess acid is evaporated off in vacuo, the residue is taken up in water, the solution is made basic with sodium bicarbonate and extracted with ethyl acetate, the organic phase is washed once more with water, dried and concentrated, and the product is rapidly reacted further.

Yield: 1.8 g (95%) of oily product.

The following are obtained by an analogous route:

n-Octyl (1RS,3RS,5RS)-2-azabicyclo[3.3.0]-7-octene-3carboxylate;

S-Proline n-octyl ester.

7) 2-tert.Butyloxycarbonyl-(1RS,3RS,5RS)-2-azabicyclo[3.3.0]-7-octene-3-carboxylic acid 6.26 g (28.7 mmol) of di-tert.-butyl dicarbonate are added, while cooling in ice, to 4.0 g (26.1 mmol) of (1RS,3RS,5RS)-2-azabicyclo[3.3.0]-7-octene-3-carboxylic acid (cis-endo racemate) in a mixture of 78 ml of dioxane/water 2:1 and 26.1 ml of 1 N sodium hydroxide solution, and the mixture is stirred at room temperature for one hour, keeping the pH continuously at pH 9 by addition of 1 N sodium hydroxide solution. The reaction solution is concentrated, the residue is dissolved in water, ethyl acetate is poured on, and the pH is adjusted to 2 with saturated potassium bisulfate solution. The phases are separated, the aqueous phase is extracted twice more with ethyl acetate, and the combined organic phases are washed with water and saturated sodium chloride solution, dried and concentrated.

Yield: 6.3 g (96%).

8) 3-Octynyl methanesulfonate 7.47 g (65 mmol) of methanesulfonyl chloride are added dropwise within 30 minutes at 10° C. to a solution of 7.56 g (60 mmol) of 3-octyn-1-ol and 12.45 ml (90mmol) triethylamine in 225 ml of methylene chloride, and the mixture is stirred for one hour. The reaction solution is washed with water, saturated sodium bicarbonate solution and again with water, dried and concentrated.

Yield: 11.9 g (97%) of oily product.

B. FINAL PRODUCTS

Example 9 n-Octyl 2-[N-(1S-ethoxycarbonyl-3-phenyl-propyl)-S-alanyl]-(1S,3S,5S)-2-azabicyclo[3.3.0]-octane-3-carboxylate 2.07 g (5 mmol) of 2-[N-(1S-ethoxycarbonyl-3-phenyl-propyl)-S-alanyl]-(1S,3S,5S)-2-azabicyclo[3.3.0]octane-3-carboxylic acid (ramipril) and 0.50 g (5 mmol) of potassium bicarbonate are stirred in 25 ml of dimethylformamide at 40° C. for 1.5 hours and, after cooling to room temperature, a solution of 1.16 g (6 mmol) of 1-bromooctane in 20 ml of dimethylformamide is added dropwise, and the mixture is stirred at room temperature overnight. The pH is adjusted to 6 by addition of 0.1 N HCl, the mixture is diluted with water and extracted three times with methylene chloride, and the combined organic phases are dried, concentrated and purified by column chromatography on 120 g of silica gel (mobile phase toluene/ethanol 95:5).

Yield: 2.35 g (89%) of oily product;
$[\alpha]_D^{25} = -23.9°$ (c=1, methanol).

Example 10 n-Octyl 2-[N-(1S-ethoxycarbonyl-3-phenylpropyl)-S-alanyl]-(1S,3S,5S)-2-azabicyclo[3.3.0]octane-3carboxylate hydrogen maleate 528 mg (1 mmol) of an amine obtained as in Example 9 are dissolved in 20 ml of ether, and a solution of 116 mg 1 mmol) of maleic acid in 4 ml of acetone is added. The solvents are evaporated off, and the residue is crystallized using diisopropyl ether.

Yield: 0.51 g (79%) of colorless crystals,
melting point 89°-90° C.

Example 11

2-Octynyl 2-[N-(1S-ethoxycarbonyl-3-phenylpropyl)-S-alanyl]-(1S,3S,5S)-2-azabicyclo[3.3.0]octane-3-carboxylate hydrogen maleate 2.08 g (5 mmol) of 2-[N-(1S-ethoxycarbonyl-3-phenyl-propyl)-S-alanyl]-(1S,3S,5S)-2-azabicyclo[3.3.0]octane-3-carboxylic acid (ramipril) and 1.00 g (10 mmol) of potassium bicarbonate are stirred in 25 ml of dimethylformamide at 40° C. for 1.5 hours, cooled to 0° C., and a solution of 2.3 g (12 mmol) of E-1-bromo-2-octene in 20 ml of dimethylformamide is added dropwise. The reaction solution is stirred at 0° C. for 4 hours, poured into 500 ml of water and extracted three times with ethyl acetate, the combined extracts are washed twice with saturated sodium bicarbonate solution and three times with water, dried and concentrated, and the crude product (3.4 g) is purified by flash chromatography on 125 g of silica gel (mobile phase cyclohexane/ethyl acetate 8:2 and 1:1).

1.93 g (73%) of an oily product are obtained and converted into the hydrogen maleate in analogy to Example 10.

Yield: 2.0 g of colorless crystals, melting point 81°-84° C.

Example 12

3-Octynyl 2-[N-(1S-ethoxycarbonyl-3-phenylpropyl)-S-alanyl]-(1S,3S,5S)-2-azabicyclo[3.3.0]octane-3-carboxylate hydrogen maleate 4.9 g (11.8 mmol) of 2-[N-(1S-ethoxycarbonyl-3-phenyl-propyl)-S-alanyl]-(1S,3S,5S)-2-azabicyclo[3.3.0]octane3-carboxylic acid (ramipril) and 2.4 g (23.6 mmol) of potassium bicarbonate are stirred in 90 ml of dimethylformamide at 40° C. for 2 hours, then a solution of 2.41 g (11.8 mmol) of the mesylate from Example 8 in 30 ml of dimethylformamide is added, and the mixture is stirred at 40° C. for a further 9 hours. The reaction solution is diluted with 250 ml of water and extracted three times with ethyl acetate, the combined organic phases are washed with saturated sodium bicarbonate solution and with water, dried and concentrated, and the crude product (5.6 g) is purified by chromatography on 200 g of silica gel (mobile phase toluene/ethanol 99:1). 3.45 g (56%) of an oily product are obtained, and 1.3 g of this are converted into the hydrogen maleate in analogy to Example 10.

Yield: 0.8 g of colorless crystals, melting point 68°-70° C.

Example 13

25 Ethyl 2-[N-(1S-n-octyloxycarbonyl-3-phenylpropyl)-S-alanyl]-(1S,3S,5S)-2-azabicyclo[3.3.0]octane-3carboxylate hydrogen maleate 1.43 g (2.8 mmol) of the carboxylic acid from Example 19 are stirred in 25 ml of ethanolic hydrochloric acid at room temperature. After 5 days, a further 25 ml of ethanolic hydrochloric acid are added, the mixture is stirred overnight and concentrated, the residue is taken up in ethyl acetate, washed three times with saturated sodium bicarbonate solution and once with water, dried and concentrated, and the crude product (1.16 g) is purified by flash chromatography on 80 g of silica gel, (mobile phase toluene/ethanol 99:1). 0.62 g (42%) of oily product are obtained and converted into the hydrogen maleate in analogy to Example 10.

Yield: 0.50 g of colorless crystals, melting point 84°-86° C.

Example 14

5-Nonyl 2-[N-(1S-ethoxycarbonyl-3-phenylpropyl)-S-alanyl]-(1S,3S,5S)-2-azabicyclo[3.3.0]octane-3--carboxylate hydrogen maleate A solution of 1.31 g (7.5 mmol) of diethyl azodicarboxylate in 10 ml of absolute tetrahydrofuran is added dropwise at 0° C. to a solution of 1.97 g (7.5 mmol) of triphenylphosphine and 0.72 g (5 mmol) of 5-nonanol in 100 ml of absolute tetrahydrofuran, the mixture is stirred for 10 minutes and then, at 0° C., a solution of 2.08 g (5 mmol) of 2-[N-(1S-ethoxycarbonyl-3-phenyl-propyl)-S-alanyl](1S,3S,5S)-2-azabicyclo[3.3.0]octane-3-carboxyic acid (ramipril) in 25 ml of absolute tetrahydrofuran is added, and the mixture is stirred at 0° C. for one hour and at room temperature overnight. The reaction solution is concentrated, the residue is taken up in ethyl acetate, the solution is washed twice with 2 N sodium hydroxide solution and once with water, dried and concentrated, and the crude product (5.0 g) is purified by flash chromatography twice on 200 g of silica gel (mobile phase a) toluene/ethanol 99:1, b) methylene chloride/ethyl acetate 9:1). The product obtained in this way (1.74 g, 64%) is converted into the hydrogen maleate in analogy to Example 10.

Yield: 1.6 g (49%); melting point 103°-105° C.

Example 15

Benzhydryl 2-[N-(1S-menthyloxycarbonyl-3-phenylpropyl)-S-alanyl]-(1S 3S 5S)-2-azabicyclo[3.3.0]octane-3-carboxylate A solution of 0.59 g (3 mmol) of benzophenone hydrazone in 12 ml of ether is added dropwise at room temperature to a suspension of 2.95 g of nickel peroxide hydrate in 12 ml of ether, the mixture is stirred for one hour and the violet solution is filtered with suction through Celite and concentrated. The 3 mmol of diphenyldiazomethane obtained in this way are dissolved in 32 ml of absolute acetone and, while cooling in ice, added dropwise to a solution of 1.31 g (2.5 mmol) of 2-[N-(1S -menthyloxycarbonyl-3-phenylpropyl)-S-alanyl]-(1S,3S,5S)2-azabicyclo[3.3.0]octane-3-carboxylic acid (see Example 45) in 32 ml of absolute acetone. The mixture is then stirred at room temperature for 38 hours and concentrated, and the crude product is purified by column chromatography on silica gel (mobile phase toluene/ethanol 99.5:0.5 and cyclohexane/ethyl acetate 8:2).

Yield: 1.63 g (95%) of oily product;
$[\alpha]_D^{25} = -57.9°$ (c=1, methanol).

Example 16 n-Octyl 2-[N-(3-cyclohexyl-1S-ethoxycarbonylpropyl)-S-alanyl]-(1S,3S,5S)-2-azabicyclo[3.3.0]octane-3-carboxylate 1.8 g (6.7 mmol) of the octyl ester from Example 6d), 1.92 g (6.7 mmol) of N-(3-cyclohexyl-1S-ethoxycarbonylpropyl) -S-alanine and 4.6 ml of absolute triethylamine are dissolved in 30 ml of absolute dimethylformamide, cooled to −5° C. and 6.7 ml of a 50% strength solution of propanephosphonic anhydride in methylene chloride is slowly added dropwise The reaction solution is stirred at room temperature overnight, poured into 200 ml of water and extracted three times with ethyl acetate, the combined organic phases are washed with water, 10% strength citric acid solution, saturated sodium carbonate solution and saturated sodium chloride solution, dried and concentrated, and the crude product (3.1 g) is purified by flash chromatograpy on 120 g of silica gel (mobile phase toluene/ethanol 199:1).

Yield: 2.48 g (69%) of colorless oil,
$[\alpha]_D^{25} = -26.4°$ (c=1, methanol).

Example 17

Benzyl 2-[N-(1S-ethoxycarbonyl-n-tridecyl)-S-phenylalanyl]-(1S,3S,5S)-2-azabicyclo[3.3.0]octane-3-carboxylate 3.5 ml (25 mmol) of absolute triethylamine and 5.0 ml of a 50% strength solution of propanephosphonic anhydride in methylene chloride are successively added dropwise to a solution of 2.1 g (5 mmol) of N-(1S-ethoxycarbonyl-n-tridecyl) -S-phenylalanine and 1.4 g (5 mmol) of benzyl (1S,3S,5S)-2-azabicyclo[3.3.0]octane-3-carboxylate in 80 ml of absolute dimethylformamide, and the reaction solution is stirred at room temperature overnight. It is then poured into water and extracted several times with ethyl acetate, the combined extracts are washed with water, 10% citric acid solution, saturated sodium bicarbonate solution and saturated sodium chloride solution, dried and concentrated, and the crude product (3.15 g) is purified by flash chromatography on silica gel (mobile phase cyclohexane/ethyl acetate 7:3).

Yield: 2.76 g (85%) of oily product
$[\alpha]_D^{20} = -8.0°$ (c=0.97, ethanol).

Example 18

Benzyl 2-[N-(1S-n-octyloxycarbonyl-3-phenylpropyl)-S-alanyl]-(1S,3S,5S)-2-azabicyclo[3.3.0]octane-3-carboxylate 6 0 ml (43.4 mmol) of absolute triethylamine and 9.2 g of n-octyl 4-phenyl-2R-(trifluoromethanesulfonyloxy)butyrate, dissolved in 20 ml of absolute methylene chloride, are successively added dropwise at 0° C. to a solution of 9.3 g (21.7 mmol) of the trifluoroacetate from Example 3b) in 100 ml of absolute methylene chloride. The mixture is allowed to reach room temperature, then stirred for 2.5 hours, extracted three times with water, dried and concentrated, and the crude product (11.4 g) is purified by flash chromatography on 450 g of silica gel (mobile phase cyclohexane/ethyl acetate 9:1, 8:2, 7:3).

Yield: 6.95 g (54%) of oily product.
$[\alpha]_D^{25} = -35.1°$ (c=1, methanol).

Example 19 tert.Butylammonium 2-[N-(1S-n-octyloxycarbonyl-3-phenylpropyl) -S-alanyl]-(1S,3S,5S)-2-azbicyclo[3.3.0]octane-3carboxylate 5.45 g (9.2 mmol) of the benzyl ester from Example 18 in 300 ml of ethanol are hydrogenated on 1 g of palladium/ charcoal (10%) at room temperature for 20 minutes. Removal of the catalyst by filtration with suction and concentration result in 4.1 g (89%) of 2-[N-(1S-n-octyloxycarbonyl -3-phenylpropyl)-S-alanyl]-(1S,3S,5S)-2azabicyclo[3.3.0]octane-3-carboxylic acid.

190 mg of tert.butylamine are added to 1.3 g of this acid in ethanol, the solvent is evaporated off, and the residue is crystallized with diisopropyl ether.

Yield: 1.27 g (86%) of colorless crystals.
melting point 141°-143° C.

Example 20 n-Octyl 2-[N-(1S-carboxy-3-phenylpropyl)-S-alanyl](1S,3S,5S)-2-azabicyclo[3.3.0]octane-3-carboxylate 2.65 g (5 mmol) of the ethyl ester from Example 9 are dissolved in 18 ml of tetrahydrofuran, 7.5 ml of 1 N sodium hydroxide solution are added, and the mixture is stirred at room temperature for 48 h. It is neutralized by addition of 7.5 ml of 1 N hydrochloric acid. The reaction mixture is concentrated, the residue is suspended in water and extracted twice with ethyl acetate, and the combined organic phases are washed with saturated sodium chloride solution, dried and concentrated, and the crude product (2.05 g) is purified by chromatography on 80 g of silica gel (toluene/ethanol 9:1). The product obtained in this way (1.15 g; 46%) is triturated in 50 ml of petroleum ether, placed in the cold, filtered off with suction and dried.

Yield: 0.83 g of colorless crystals; melting point 56°–61° C.

The following compounds according to the invention are also obtained by using suitable starting materials and employing the processes described in Examples 9–20:

Example 21 n-Octyl 2-[N-(1S-ethoxycarbonyl-n-heptyl)-S-alanyl](1S,3S,5S)-2-azabicyclo[3.3.0]octane-3-carboxylate

Example 22 n-Decyl 2-[N-(1S-ethoxycarbonyl-3-phenylpropyl)-S-alanyl]-(1S,3S,5S)-2-azabicyclo[3.3.0]octane-3carboxylate; $[\alpha]_D^{25} = -25.8°$ (c=1, methanol)

Example 23 n-Tetradecyl 2-[N-(1S-ethoxycarbonyl-3-phenylpropyl)-S-alanyl]-(1S,3S,5S)-2-azabicyclo[3.3.0]octane-3carboxylate; $[\alpha]_D^{25} = -19.8°$ (c=1, methanol).

2-Octynyl 2-[N-(1S-ethoxycarbonyl-3-phenylpropyl)-S-alanyl]-(1S,3S,5S)-2-azabicyclo[3.3.0]octane-3carboxylate hydrogen maleate; melting point 70°–72° C.

Example 25 n-Octyl 2-[N-(1S-isobutyloxycarbonyl-3-phenylpropyl)-S-alanyl]-(1S,3S,5S)-2-azabicyclo[3.3.0]octane-3carboxylate; $[\alpha]_D^{25} = -23.7°$ (c=1, methanol).

Example 26 n-Octyl 2-[N-(1S-n-octyloxyycarbonyl-3-phenylpropyl)-S-alanyl]-(1S,3S,5S)-2-azabicyclo[3.3.0]octane-3carboxylate; $[\alpha]_D^{25} = -18.6°$ (c=1, methanol).

Example 27 n-Octyl 2-[N-(1S-n-octadecyloxycarbonyl-3-phenylpropyl) -S-alanyl]-(1S,3S,5S)-2-azabicyclo[3.3.0]octane-3carboxylate; $[\alpha]_D^{25} = -15.2°$ (c=1, methanol).

Example 28 n-Octyl 1'-[N-(1S-ethoxycarbonyl-3-phenylpropyl)-S-alanyl]-spiro[bicyclo[2.2.2]octane-2,3'-pyrrolidine]-5'S-carboxylate;

Example 29 n-Nonyl 1'-[N-(1S-ethoxycarbonyl-3-phenylpropyl)-S-alanyl]-spiro[bicyclo[2.2.2]octane-2,3'-pyrrolidine]-5'-S-carboxylate hydrogen maleate; melting point 110° C.

Example 30 n-Decyl 1'-[N-(1S-ethoxycarbonyl-3-phenylpropyl)-S-alanyl]-spiro[bicyclo[2.2.2]octane-2,3'-pyrrolidine]-5'S-carboxylate hydrogen maleate; melting point 96° C.

Example 31 n-Octyl 2-[N-(1S-ethoxycarbonyl-3-phenylpropyl)-S-alanyl]-(1R,3R,5R)-2-azabicyclo[3.3.0]octane-3-carboxylate; $[\alpha]_D^{25} = -7.0°$ (c=1, methanol).

Example 32 n-Octyl 2-[N-(1S-ethoxycarbonyl-3-phenylpropyl)-R-alanyl]-(1S,3S,5S)-2-azabicyclo[3.3.0]octane-3carboxylate; $[\alpha]_D^{25} = +18.0°$ (c=1, methanol).

Example 33 n-Octyl 2-[N-(1R-ethoxycarbonyl-3-phenylpropyl)-R-alanyl]-(1S,3S,5S)-2-azabicyclo[3.3.0]octane-3-carboxylate; $[\alpha]_D^{25} = +9.4°$ (c=1, methanol).

Example 34 n-Octyl 2-[N-(1S-ethoxycarbony13-phenylpropyl)-S-alanyl]-(1S,3S,5S)-2-azabicyclo[3.3.0]-7-octene-3carboxylate; $[\alpha]_D^{25} = +21.2°$ (c=1, methanol).

Example 35 n-Octyl 2-[N-(1S-ethoxycarbonyl-3-phenylpropyl)-S-alanyl]-(1R,3R,5R)-2-azabicyclo[3.3.0]-7-octene-3-carboxylate; $[\alpha]_D^{25} = -51.4°$ (c=1, methanol).

Example 36

N-[N'-(1S-Ethoxycarbonyl-3-phenylpropyl)-S-alanyl]-S-proline n-octyl ester hydrogen maleate; melting point 105°–107° C.

Example 37

2-[N-(1S-Ethoxycarbonyl-n-tridecyl)-S-phenylalanyl]-(1S,3S,5S)-2-azabicyclo[3.3.0]octane-3-carboxylic acid; $[\alpha]_D^{20} = +27.2°$ (c=1, methanol).

Example 38

Benzyl 2-[N-(1S-Ethoxycarbonyl-n-tridecyl)-S-alanyl](1S,3S,5S)-2-azabicyclo[3.3.0]octane-3-carboxylate;

Example 39

Benzyl 2-[N-(1R-Ethoxycarbonyl-n-tridecyl)-S-alanyl](1S,3S,5S)-2-azabicyclo[3.3.0]octane-3-carboxylate;

Example 40

Benzyl 2-[N-(1S-Octadecyloxycarbonyl-3-phenylpropyl)-S-alanyl]-(1S,3S,5S)-2-azabicyclo[3.3.0]octane-3carboxylate; $[\alpha]_D^{25} = -28.6°$ (c=1, methanol)

Example 41

Benzyl 2-[N-(1S-Menthyloxycarbonyl-3-phenylpropyl)-S-alanyl]-(1S,3S,5S)-2-azabicyclo[3.3.0]octane-3-carboxylate; $[\alpha]_D^{25} = -63.2°$ (c=1, methanol)

Example 42

3,3-Diphenylnpropyl 2-[N-(1S-ethoxycarbonyl-3-phenylpropyl) -S-alanyl]-(1S,3S,5S)-2-azabicyclo[3.3.0]-octane3-carboxylate hydrogen maleate; melting point 122°-124° C.

Example 43

5-Nonyl 1'-[N-(1S-ethoxycarbonyl-3-phenylpropyl)-S-alanyl]-spiro[bicyclo[2.2.2]octane-2,3'-pyrrolidine)-5'S-carboxylate hydrogen maleate, melting point 121° C.

Example 44 tert.Butylammonium 2-[N-(1S-octadecyloxycarbonyl-3-phenylpropyl) -S-alanyl]-(1S,3S,5S)-2-azabicyclo[3.3.0]-octane-3-carboxylate; melting point 133°-135° C.

Example 45 tert.Butylammonium 2-[N-(1S-menthyloxycarbonyl-3-phenylpropyl) -S-alanyl]-(1S,3S,5S)-2-azabicyclo[3.3.0]-octane-3-carboxylate; melting point 164°-167° C.

Example 46 n-Octyl 2-[N-(1R-ethoxycarbonyl-3-phenylpropyl)-S-alanyl]-(1S,3S,5S)-2-azabicyclo[3.3.0]octane-3carboxylate; $[\alpha]_D^{25} = -30.8°$ (c=1, methanol).

Example 47 n-Octyl 2-[N-(1R-ethoxycarbonyl-3-phenylpropyl)-R-alanyl]-(1R,3R,5R)-2-azabicyclo[3.3.0]octane-3carboxylate hydrogen maleate; melting point 89°-91° C.

Example 48 n-Octyl 2-[N-(1S-methoxycarbonyl-3-phenylpropyl)-S-alanyl]-(1S,3S,5S)-2-azabicyclo[3.3.0]octane-3-carboxylate; $[\alpha]_D^{25}, = -18.0$ (c=1, methanol).

Example 49 n-Octyl 2-[N-(1S-benzyloxycarbonyl-3-phenylpropyl)-S-alanyl]-(1S,3S,5S)-2-azabicyclo[3.3.0]octane-3carboxylate; $[\alpha]_D^{25}, = -34.3°$ (c=1, methanol).

Example 50 n-Decyl 2-[N-(1S-carboxy-3-phenylpropyl)-S-alanyl]-(1S,3S,5S)-2-azabicyclo[3.3.0]octane-3-carboxylate, melting point 52°.

What is claimed is:
1. A compound of the formula I

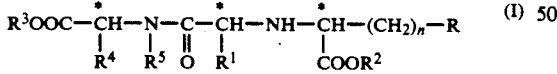

in which
n is 2,
R denotes an aliphatic radical having 1–18 carbon atoms, an alicyclic radical having 3–20 carbon atoms, or an aromatic radical having 6–12 carbon atoms,
$R^1$ denotes the side-chain, which is protected if necessary, of a naturally occurring α-amino acid of the formula $R^1$—CH(NH₂)—COOH,
$R^2$ denotes hydrogen, an aliphatic radical having 1–18 carbon atoms, benzyl or an alicyclic radical having 3–20 carbon atoms,
$R^3$ denotes hydrogen, an aliphatic radical having 1–18 carbon atoms or an araliphatic radical having 7–20 carbon atoms, and $R^4$ and $R^5$ form, together with the atoms carrying them, a ring system which is an octahydrocyclopenta[b]pyrrole, sprio [(bicyclo[2.2.2]octane)-2,3'-pyrrolidine], pyrrolidine or 1,2,3,3a,4,6a-hexahydrocyclopenta[b]pyrrole ring system,
with the proviso that
A: $R^2$ denotes an aliphatic radical having 7–18 carbon atoms or an alicyclic radical having 7–20 carbon atoms, and otherwise n, R, $R^1$, $R^3$, $R^4$ and $R^5$ have the above-mentioned meaning, or
B: $R^3$ denotes an aliphatic radical having 7–18 carbon atoms or an araliphatic radical having 8–20 carbon atoms, and otherwise n, R, $R^1$, $R^2$, $R^4$ and $R^5$ have the above-mentioned meaning, or
C: R denotes an aliphatic radical having 9–18 carbon atoms, and otherwise n, $R^1$, $R^2$, $R^3$, $R^4$ and $R^5$ have the above-mentioned meaning,
or a physiologically tolerated salt thereof, excepting n-octyl 2-[N-(1S-ethoxycarbonyl-3-phenylpropyl)-S-alanyl]-(1S,3S,5S)-2-azabicyclo[3.3.0]octane-3-carboxylate, n-octyl 2-[N-(1S-carboxyl-3-phenylpropyl)-S-alanyl]-(1S,3S,5S)-2-azabicyclo[3.3.0]octane-3-carboxylate, and the physiologically tolerated salts thereof;
and wherein said aliphatic radicals are aliphatic acrylic radicals having an open, straight or branched, saturated or unsaturated carbon chain; said alicyclic radicals are isocyclic non-aromatic radicals which may carry open-chain aliphatic side-chains, which radicals may be linked via a ring carbon atom or a side-chain carbon atom, and which may contain one or more rings; and said araliphatic radicals are aromatic-aliphatic radicals;
and further, wherein the following compounds, and salts thereof, are excluded:
(i) where $R^4$ and $R^5$ form, together with the atoms carrying them, an octahydrocyclopenta[b]pyrrole ring system, those compounds where, also, (a) R is phenyl, $R^1$ is methyl, $R^2$ is ethyl and $R^3$ is octadecyl, benzhydryl or 3-phenyl-n-propyl, (b) R is phenyl, $R^1$ is methyl, $R^2$ is isobutyl and $R^3$ is benzhydryl, or (c) $R^1$ is methyl, $R^2$ is ethyl, $R^3$ is hydrogen and R is n-decyl or n-tetradecyl;
(ii) where $R^4$ and $R^5$ form, together with the atoms carrying them, a spiro [(bicyclo[2.2.2]octane)-2,3'-pyrrolidine]ring system, those compounds where, also, (a) R is phenyl, $R^1$ is methyl, $R^2$ is isobutyl and $R^3$ is benzhydryl, (b) R is n-decyl, $R^1$ is methyl, $R^2$ is ethyl and $R^3$ is hydrogen, or (c) R is phenyl, $R^1$ is methyl, $R^2$ is ethyl and $R^3$ is benzhydryl or 8-phenyl-n-octyl;
(iii) where $R^4$ and $R^5$ form, together with the atoms carrying them, a pyrrolidine ring, those compounds where, also, (a) $R^1$ is methyl, $R^2$ is ethyl, $R^3$ is hydrogen and R is n-decyl or n-tetradecyl, (b) R is phenyl, $R^1$ is methyl, $R^2$ is ethyl and $R^3$ is 2-phenylethyl, or (c) R is phenyl, $R^1$ is methyl, $R^2$ is isopropyl and $R^3$ is benzhydryl; and
(iv) where $R^4$ and $R^5$ form, together with the atoms carrying them, a 1,2,3,3a,4,6a-hexahydrocyclopenta[b]pyrrole ring system, those compounds where, also, $R^1$ is methyl, $R^2$ is ethyl, $R^3$ is hydrogen and R is n-decyl or n-tetradecyl.

2. A compound of the formula I as claimed in claim 1, in which
n is 2
R denotes an aliphatic radical having 4–10 carbon atoms, an alicyclic radical having 6 carbon atoms or an aromatic radical having 6 carbon atoms, $R^1$ denotes methyl or benzyl, $R^2$ denotes hydrogen, an aliphatic radical having 1-18 carbon atoms, benzyl or an alicyclic radical having 6-10 carbon atoms, and $R^3$ denotes hydrogen, an aliphatic radical having 2-14 carbon atoms or an araliphatic radical having 8 to 15 carbon atoms, with the proviso that A: $R^2$ denotes an aliphatic radical having 7-18 carbon atoms or an alicyclic radical having 7-10 carbon atoms, and otherwise n, R, $R^1$, $R^3$, $R^4$ and $R^5$ have the abovementioned meaning, or B: $R^3$ denotes an aliphatic radical having 7-14 carbon atoms or an araliphatic radical having 7-15 carbon atoms, and otherwise n, R, $R^1$, $R^2$, $R^4$ and $R^5$ have the abovementioned meaning, or C: R denotes an aliphatic radical having 9 or 10 carbon atoms, and otherwise n, $R^1$, $R^2$, $R^3$, $R^4$ and $R^5$ have the abovementioned meaning, or a physiologically tolerated salt thereof.

3. A compound of the formula I as claimed in claim 1, in which n is 2,

R denotes n-butyl, n-decyl, cyclohexyl or phenyl, $R^1$ denotes methyl or benzyl, $R^2$ denotes hydrogen, methyl, ethyl, isobutyl, n-octyl, n-octadecyl, benzyl or menthyl, $R^3$ denotes hydrogen, ethyl, n-octyl, n-nonyl, 5-nonyl, n-decyl, n-tetradecyl, 2-octenyl, 2-octynyl, 3octynyl, benzyl, benzhydryl or 3,3-diphenylpropyl, with the proviso that A: $R^2$ denotes n-octyl, n-octadecyl or menthyl, and otherwise n, R, $R^1$, $R^3$, $R^4$ and $R^5$ have the abovementioned meaning, or B: $R^3$ denotes n-octyl, n-nonyl, 5-nonyl, n-decyl, n-tetradecyl, 2-octenyl, 2-octynyl, 3-octynyl, benzhydryl or 3,3-diphenylpropyl, and otherwise n, R, $R^1$, $R^2$, $R^4$ and $R^5$ have the abovementioned meaning, or C: R denotes n-decyl, and otherwise n, $R^1$, $R^2$, $R^3$, $R^4$ and $R^5$ have the stated meaning, or a physiologically tolerated salt thereof.

4. A compound of the formula I as claimed in claim 1, selected from the group of compounds n-Octyl 2-[N-(1S-ethoxycarbonyl-n-heptyl)-S-alanyl](1S,3S,5S)-2-azabicyclo[3.3.0]octane-3-carboxylate;

n-Octyl 2-[N-(1S-ethoxycarbonyl-3-cyclohexylpropyl)-S-alanyl]-(1S,3S,5S)-2-azabicyclo[3.3.0]octane-3carboxylate;

Benzyl 2-[N-(1S-ethoxycarbonyl-n-tridecyl)-S-alanyl](1S,3S,5S)-2-azabicyclo[3.3.0]octane-3-carboxylate;

Benzyl 2-[N-(1R-ethoxycarbonyl-n-tridecyl)-S-alanyl](1S,3S,5S)-2-azabicyclo[3.3.0]octane-3-carboxylate;

n-Decyl 2-[N-(1S-ethoxycarbonyl-3-phenylpropyl)-S-alanyl]-(1S,3S,5S)-2-azabicyclo[3.3.0]octane-3-carboxylate;

5-Nonyl 2-[N-(1S-ethoxycarbony-)-3-phenylpropyl)-S-alanyl]-(1S,3S,5S)-2-azabicyclo[3.3.0]octane-3carboxylate;

n-Octyl 2-[N-(1S-isobutyloxycarbonyl-3-phenylpropyl)-S-alanyl]-(1S,3S,5S)-2-azabicyclo[3.3.0]octane-3carboxylate;

2-[N-(1S-n-octyloxycarbonyl-3-phenylpropyl)-S-alanyl]-(1S,3S,5S)-2-azabicyclo[3.3.0]octane-3carboxylate acid;

Ethyl 2-[N-(1S-n-octyloxycarbonyl-3-phenylpropyl)-S-alanyl]-(1S,3S,5S)-2-azabicyclo[3.3.0]octane-3-carboxylate;

n-Octyl 2-[N-(1S-n-octyloxycarbonyl-3-phenylpropyl)-S-alanyl]-(1S,3S,5S)-2-azabicyclo[3.3.0]octane-3carboxylate;

Benzyl 2-[N-(1S-n-octadecyloxycarbonyl-3-phenylpropyl)-S-alanyl]-(1S,3S,5S)-2-azabicyclo[3.3.0]octane-3carboxylate;

n-Octyl 2-[N-(1S-n-octadecyloxycarbonyl-3-phenylpropyl)-S-alanyl] -(1S,3S,5S)-2-azabicyclo[3.3.0]octane-3carboxylate;

Benzyl 2-[N-(1S-menthyloxycarbonyl-3-phenylpropyl)-S-alanyl]-(1S,3S,5S)-2-azabicyclo[3.3.0]octane-3-carboxylate;

Benzhydryl 2-[N-(1S-menthyloxycarbonyl-3-phenylpropyl)-S-alanyl]-(1S,3S,5S)-2-azabicyclo[3.3.0]octane-3carboxylate;

n-Octyl 2-[N-(1S-ethoxycarbonyl-3-phenylpropyl)-S-alanyl]-(1S,3S,5S)-2-azabicyclo[3.3.0]-7-octene-3carboxylate;

N-[N-(1S-ethoxycarbonyl-3-phenylpropyl)-S-alanyl]-S-proline n-octyl ester;

n-Octyl 2-[N-(1S-methoxycarbonyl-3-phenylpropyl)-S-alanyl]-(1S,3S,5S)-2-azabicyclo[3.3.0]octane-3carboxylate;

n-Octyl 2-[N-(1S-benzyloxycarbonyl-3-phenylpropyl)-S-alanyl]-(1S,3S,5S)-2-azabicyclo[3.3.0]octane-3carboxylate;

n-Decyl 2-[N-(1S-carboxy-3-phenylpropyl)-S-alanyl](1S,3S,5S)-2-azabicyclo[3.3.0]octane-3-carboxylate, or a physiologically tolerated salt thereof.

5. A method for the treatment of at least one cognitive dysfunction, comprising the step of administering to a mammal in need thereof and for the purpose of said treatment, an effective amount of a compound of the following formula I:

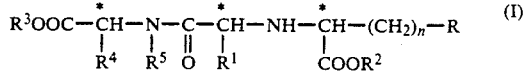

in which n is 2,

R denotes an aliphatic radical having 1-18 carbon atoms, an alicyclic radical having 3-20 carbon atoms, or an aromatic radical having 6-12 carbon atoms, $R^1$ denotes the side-chain, which is protected if necessary, of a naturally occurring α-amino acid of the formula $R^1$—CH(NH$_2$)—COOH, $R^2$ denotes hydrogen, an aliphatic radical having 1-18 carbon atoms, benzyl or an alicyclic radical having 3-20 carbon atoms, $R^3$ denotes hydrogen, an aliphatic radical having 1-18 carbon atoms or an araliphatic radical having 7-20 carbon atoms, and $R^4$ and $R^5$ form, together with the atoms carrying them, a ring system which is an octahydrocyclopenta[b]pyrrole, spiro[(bicyclo[2.2.2]octane)-2,3'-pyrrolidine], pyrrolidine or 1,2,3,3a,4,6a-hexahydrocyclopenta[b]pyrrole ring system, with the proviso that A: R² denotes an aliphatic radical having 7-18 carbon atoms or an alicyclic radical having 7-20 carbon atoms, and otherwise n, R, R¹, R³, R⁴ and R⁵ have the abovementioned meaning, or B: R³ denotes an aliphatic radical having 7-18 carbon atoms or an araliphatic radical having 7-20 carbon atoms, and otherwise n, R, R¹, R², R⁴ and R⁵ have the above-mentioned meaning, or C: R denotes an aliphatic radical having 9-18 carbon atoms, and otherwise n, R¹, R², R³, R⁴ and R⁵ have the above-mentioned meaning, a physiologically tolerated salt thereof, excepting n-octyl 2-[N-(1S-ethoxycarbonyl-3-phenylpropyl)-S-alanyl]-(1S,3S,5S)-2-azabicyclo[3.3.0]octane-3-carboxylate, n-octyl 2-[N-(1S-carboxyl-3-phenylpropyl)-S-alanyl]-(1S,3S,5S)-2-azabicyclo[3.3.0]octane-3-carboxylate, and the physiologically tolerated salts thereof;

and wherein said aliphatic radicals are aliphatic acrylic radicals having an open, straight or branched, saturated or unsaturated carbon chain; said alicyclic radicals are isocyclic non-aromatic radicals which may carry open-chain aliphatic side-chains, which radicals may be linked via a ring carbon atom or a side-chain carbon atom, and which may contain one or more rings; and said araliphatic radicals are aromatic-aliphatic radicals;

and further, wherein the following compounds, and salts thereof, are excluded:

(i) where R⁴ and R⁵ form, together with the atoms carrying them, an octahydrocyclopenta[b]pyrrole ring system, those compounds where, also, (a) R is phenyl, R¹ is methyl, R² is ethyl and R³ is octadecyl, benzhydryl or 3-phenyl-n-propyl, (b) R is phenyl, R¹ is methyl, R² is isobutyl and R³ is benzyl or benzhydryl, (c) R¹ is methyl, R² is ethyl, R³ is hydrogen and R is n-decyl or n-tetradecyl, or (d) R is cyclohexyl, R¹ is methyl, R² is ethyl and R³ is benzyl;

(ii) where R⁴ and R⁵ form, together with the atoms carrying them, a spiro[bicyclo[2.2.2]octane)-2,3'-pyrrolidine]ring system, those compounds where, also, (a) R is phenyl, R¹ is methyl, R² is isobutyl and R³ is benzyl or benzhydryl, (b) R is n-decyl, R¹ is methyl, R² is ethyl and R³ is hydrogen, (c) R is phenyl-n-octyl, or (d) R is phenyl, R¹ is methyl, R³ is benzyl and R² is hydrogen or benzyl;

(iii) where R⁴ and R⁵ form, together with the atoms carrying them, a pyrrolidine ring, those compounds where, also, (a) R¹ is methyl, R² is ethyl, R³ is hydrogen and R is n-decyl or n-tetradecyl, (b) R is phenyl, R¹ is methyl, R² is ethyl and R³ is 2-phenylethyl, or (c) R is phenyl, R¹ is methyl, R² is isopropyl and R³ is benzhydryl; and (iv) where R⁴ and R⁵ form, together with the atoms carrying them, a 1,2,3,3a,4,6a-hexahydrocyclopenta[b]pyrrole ring system, those compounds where, also, R¹ is methyl, R² is ethyl, R³ is hydrogen and R is n-decyl or n-tetradecyl.

6. A pharmaceutical composition comprising an effective amount of a compound of the following formula I, and a physiologically acceptable vehicle:

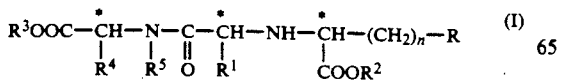

in which n is 2,

R denotes an aliphatic radical having 1-18 carbon atoms, an alicyclic radical having 3-20 carbon atoms, or an aromatic radical having 6-12 carbon atoms, R¹ denotes the side-chain, which is protected if necessary, of a naturally occurring α-amino acid of the formula R¹—CH(NH₂)—COOH, R² denotes hydrogen, an aliphatic radical having 1-18 carbon atoms, benzyl or an alicyclic radical having 3-20 carbon atoms, R³ denotes hydrogen, an aliphatic radical having 1-18 carbon atoms or an araliphatic radical having 7-20 carbon atoms, and R⁴ and R⁵ form, together with the atoms carrying them, a ring system which is an octahydrocyclopenta[b]pyrrole, spiro[(bicyclo[2.2.2]octane)-2,3'-pyrrolidine], pyrrolidine or 1,2,3,3a,4,6a-hexahydrocyclopenta[b]pyrrole ring system, with the proviso that A: R² denotes an aliphatic radical having 7-18 carbon atoms or an alicyclic radical having 7-20 carbon atoms, and otherwise n, R, R¹, R³, R⁴ and R⁵ have the above-mentioned meaning, or B: R³ denotes an aliphatic radical having 7-18 carbon atoms or an araliphatic radical having 7-20 carbon atoms, and otherwise n, R, R¹, R², R⁴ and R⁵ have the above-mentioned meaning, or C: R denotes an aliphatic radical having 9-18 carbon atoms, and otherwise n, R¹, R², R³, R⁴ and R⁵ have the above-mentioned meaning, or a physiologically tolerated salt thereof, excepting n-octyl 2-[N-(1S-ethoxycarbonyl-3-phenylpropyl)-S-alanyl]-(1S,3S,5S)-2-azabicyclo[3.3.0]octane-3-carboxylate, n-octyl 2-[N-(1S-carboxyl-3-phenylpropyl)-S-alanyl]-(1S,3S,5S)-2-azabicyclo[3.3.0]octane-3-carboxylate, and the physiologically tolerated salts thereof;

and wherein said aliphatic radicals are aliphatic acrylic radicals having an open, straight or branched, saturated or unsaturated carbon chain; said alicyclic radicals are isocyclic non-aromatic radicals which may carry open-chain aliphatic side-chains, which radicals may be linked via a ring carbon atom or a side-chain carbon atom, and which may contain one or more rings; and said araliphatic radicals are aromatic-aliphatic radicals;

and further, wherein the following compounds, and salts thereof, are excluded:

(i) where R⁴ and R⁵ form, together with the atoms carrying them, an octahydrocyclopenta[b9 pyrrole ring system, those compounds where, also, (a) R is phenyl, R¹ is methyl, R² is ethyl and R³ is octadecyl, benzhydryl or 3-phenyl-n-propyl, (b) R is phenyl, R¹ is methyl, R² is isobutyl and R³ is benzyl or benzhydryl, (c) R¹ is methyl, R² is ethyl, R³ is hydrogen and R is n-decyl or n-tetradecyl, or (d) R is cyclohexyl, R¹ is methyl, R² is ethyl and R³ is benzyl;

(ii) where R⁴ and R⁵ form, together with the atoms carrying them, a spiro[(bicyclo[2.2.2]octane)-2,3'-pyrrolidine]ring system, those compounds where, also, (a) R is phenyl, R¹ is methyl, R² is isobutyl and R³ is benzyl or benzhydryl, (b) R is n-decyl, R¹ is methyl, R² is ethyl and R³ is hydrogen, (c) R is phenyl, R¹ is methyl, R² is ethyl and R³ is benzhydryl or 8-phenyl-n-octyl, or (d) R is phenyl, R¹ is methyl, R³ is benzyl and R² is hydrogen or benzyl;

(iii) where $R^4$ and $R^5$ form, together with the atoms carrying them, a pyrrolidine ring, those compounds where, also, (a) $R^1$ is methyl, $R^2$ is ethyl, $R^3$ is hydrogen and R is n-decyl or n-tetradecyl, (b) R is phenyl, $R^1$ is methyl, $R^2$ is ethyl and $R^3$ is 2-phenylethyl, or (c) R is phenyl, $R^1$ is methyl, $R^2$ is isopropyl and $R^3$ is benzhydryl; and (iv) where $R^4$ and $R^5$ form, together with the atoms carrying them, a 1,2,3,3a,4,6a-hexahydrocyclopenta[b]pyrrole ring system, those compounds where, also, $R^1$ is methyl, $R^2$ is ethyl, $R^3$ is hydrogen and R is n-decyl or n-tetradecyl.

7. The method of claim 5, with the further proviso that, when $R^3$ is benzyl, said compound of formula I also contains an $R^2$ group selected from those within the A proviso or an R group selected from those within the C proviso.

8. The pharmaceutical composition of claim 6, with the further proviso that, when $R^3$ is benzyl, said compound of formula I also contains an $R^2$ group selected from those within the A proviso or an R group selected from those within the C proviso.

9. The compound 2-[N-(1R-ethoxycarbonyl-n-heptyl)-S-alanyl]-(1S,3S,5S)-2-azabicyclo[3.3.0]octane-3-carboxylic acid.

10. The compound 2-[N-(1S-ethoxycarbonyl-n-heptyl)-S-alanyl]-(1S,3S,5S)-2-azabicyclo[3.3.0]octane-3-carboxylic acid.

11. The compound benzyl 2-[N-(1S-ethoxycarbonyl-n-heptyl)-S-alanyl]-(1S,3S,5S)-2-azabicyclo[3.3.0]octaine-3-carboxylate.

* * * * *

UNITED STATES PATENT AND TRADEMARK OFFICE
CERTIFICATE OF CORRECTION

PATENT NO. : 5,043,346

DATED : August 27, 1991

INVENTOR(S) : Franz Hock et al.

It is certified that error appears in the above-identified patent and that said Letters Patent is hereby corrected as shown below:

Claim 1, column 22, line 25, "acrylic" should read --acyclic--.

Claim 2, column 23, line 14, "7-15" should read --8-15--.

Claim 3,, column 23, line 27, after "menthyl" insert --and--.

Claim 3, column 23, line 30, "3octynyl" should read --3-octynyl--.

Col. 24, lines 2-3, and 8-9, line 12, line 15, line 21,

"3carboxylate" should read --3-carboxylate--.

Claim 4, column 23, lines 2-3, line 12, line 15, line 21, lines 23-24, lines 28-29, and lines 31-32, "3carboxylate" should read --3-carboxylate--.

Claim 5, column 25, line 19, "acrylic" should read --acyclic--.

UNITED STATES PATENT AND TRADEMARK OFFICE
CERTIFICATE OF CORRECTION

PATENT NO. : 5,043,346

DATED : August 27, 1991

INVENTOR(S) : Franz Hock et al.

It is certified that error appears in the above-identified patent and that said Letters Patent is hereby corrected as shown below:

```
Claim 5, column 25, line 40, "octaine" should read
--octane--.
Claim 6, column 26, line 17, "octaine" should read
--octane--.
Claim 6, column 26, line 51, "[b9" should read --[b]--.
Claim 7, column 26, line 40, "acrylic" should read
--acyclic--.
Claim 11, column 28, lines 15-16, "octaine" should read
--octane--.
```

Signed and Sealed this

Twenty-second Day of June, 1993

Attest:

MICHAEL K. KIRK

Attesting Officer

Acting Commissioner of Patents and Trademarks